(12) United States Patent
Naka et al.

(10) Patent No.: US 7,623,223 B2
(45) Date of Patent: Nov. 24, 2009

(54) STRESS MEASUREMENT METHOD

(75) Inventors: Nobuyuki Naka, Kyoto (JP); Shinsuke Kashiwagi, Kyoto (JP)

(73) Assignee: HORIBA, Ltd., Kyoto (JP)

( * ) Notice: Subject to any disclaimer, the term of this patent is extended or adjusted under 35 U.S.C. 154(b) by 226 days.

(21) Appl. No.: 11/869,207

(22) Filed: Oct. 9, 2007

(65) Prior Publication Data

US 2008/0084552 A1   Apr. 10, 2008

(30) Foreign Application Priority Data

Oct. 10, 2006   (JP)   ............................ P2006-277029
Aug. 30, 2007   (JP)   ............................ P2007-224321

(51) Int. Cl.
*G01B 11/16* (2006.01)
*G01L 1/00* (2006.01)
(52) U.S. Cl. .......................................... 356/32; 702/43
(58) Field of Classification Search ............. 356/32–35, 356/237.1–237.5
See application file for complete search history.

(56) References Cited

U.S. PATENT DOCUMENTS 5,999,255 A   12/1999   Dupee et al.

2005/0259269 A1*  11/2005  Latypov et al. ............. 356/512
2007/0146685 A1*   6/2007  Yoo et al. ..................... 356/32
2008/0086276 A1*   4/2008  Naka et al. ................... 702/43

FOREIGN PATENT DOCUMENTS

| GB | 2 417 772 A | 3/2006 |
| JP | 01-219529 | 9/1989 |
| JP | 2000-009664 | 1/2000 |
| JP | 2006-073866 | 3/2006 |

* cited by examiner

*Primary Examiner*—Michael P Stafira

(57) ABSTRACT

An object of this invention is to provide stress measurement method that is stress of the measuring object nondestructively in a short period of time.

In order to attain this object, the stress measurement apparatus 1 comprises a correlation data storage section 41 that analyzes a correlation between reference stress related data obtained from a Raman spectrum L of an entire predetermined area W1 of a reference specimen W and local stress originated data as being data obtained based on a local stress each of which applies to multiple positions $WS_1$~$WS_n$ respectively in the predetermined area W1 and stores correlation data indicating the correlation, a data obtaining section 42 that obtains measurement stress related data from a Raman spectrum L on an entire measurement area W1', corresponding to the predetermined area W1, of a measurement specimen WS', and a calculation section 43 that calculates local stress originated data in the measurement area W1' based on the correlation data and the measurement stress related data.

6 Claims, 12 Drawing Sheets

Fig.8 comparison of spectrum (a)
large spot (low magnification)
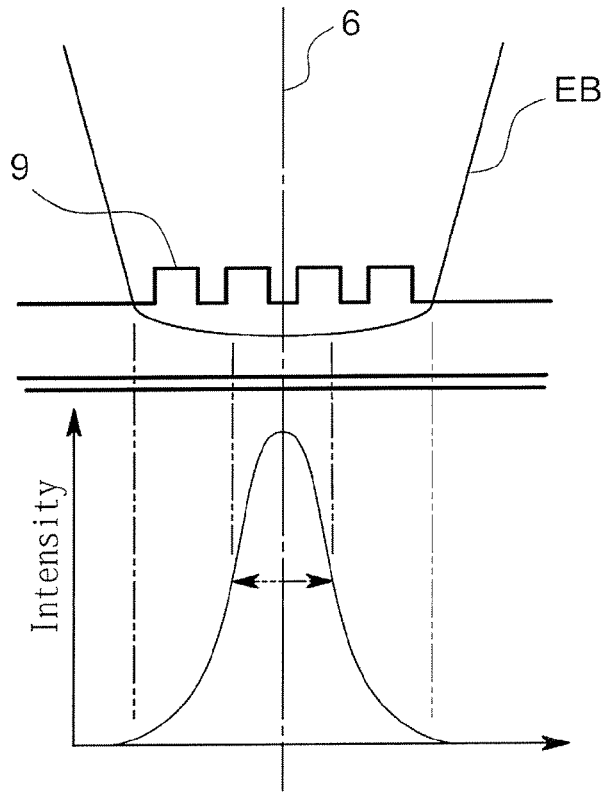
(b)
small spot (high magnification)
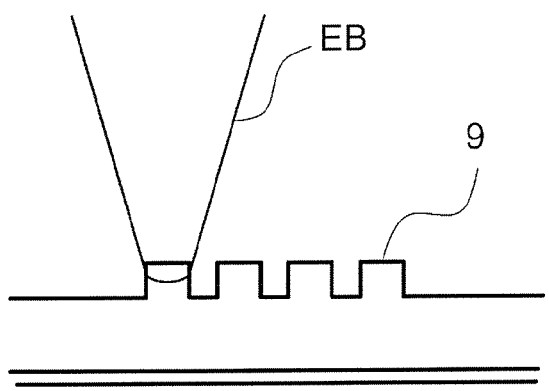
Fig.12

STRESS MEASUREMENT METHOD

BACKGROUND OF THE INVENTION AND RELATED ART STATEMENT

The present claimed invention relates to stress measurement method especially preferably used for measuring stress of a measurement specimen whose shape and composition are standardized to a certain degree such as a mass-produced semiconductor substrate and devices.

In order to measure stress applying to a specimen in a process line, it is required to measure the specimen nondestructively in a short period of time. Furthermore, in a field of, for example, semiconductor manufacturing, recently a request has been arising for measuring stress applying to micro-structures smaller than μm order or thin films accurately.

As a method for measuring stress applying to a specimen, there are the XRD (the X-ray Diffraction) and the CBED (the Convergent Beam Electron Diffraction) as shown in the patent document 1 or the patent document 2.

In accordance with the XRD, the stress can be measured without destroying the specimen. However, since the XRD has a spatial resolution of several dozen μm at most, it is difficult to measure the stress applying to a micro-structure of smaller than a μm order or a thin film accurately. Furthermore, there is a problem that it takes time to measure the stress.

In accordance with the CBED, the stress can be measured accurately by making use of a very high special resolution of smaller than 100 nm. However, since a broken measurement specimen has to be prepared separately, there are some problems such that it takes time to conduct measurement and the measurement specimen does not coincide with an actually manufactured device in a precise sense.

Accordingly, if the above-mentioned XRD or CBED is actually applied to measurement of stress in a process line, the time required for measurement becomes a big bottleneck.

On the contrary, as shown in the patent document 3, if the Raman spectroscopy is used, it becomes possible to conduct measurement in a short period of time to a degree applicable for a process line. With this method, however, a measurable area by using a microscope is about 1 μm at the minimum and an area smaller than 1 μm is difficult to measure.

More specifically, in order to measure the stress applied to a micro-structure of smaller than a μm order or a thin film, either conventional method would produce some problem in a point such as a size of a measurable area, time required for measurement, nondestructive measurement or a measurement accuracy.

Patent document 1 Japan patent laid-open number He1-219529

Patent document 2 Japan patent laid-open number 2000-009664

Patent document 3 Japan patent laid-open number 2006-73866

SUMMARY OF THE INVENTION

Then the present claimed invention intends to make it possible to measure and to accurately measure stress applying to a micro-structure of several dozen nm~μm order or a thin film with merits of the Raman spectroscopy that can conduct measurement in a short period of time nondestructively.

More specifically stress measurement method in accordance with this invention is characterized by comprising a reference stress related data obtaining step that measures a Raman spectrum by irradiating energy lines on an entire predetermined area of a reference specimen and obtains data (hereinafter called as reference stress related data) regarding stress of the entire predetermined area from the Raman spectrum, a local stress originated data obtaining step that measures local stress applying to each of multiple positions in the predetermined area and obtains local stress originated data as being data that can be obtained based on the local stress, a correlation data storage step that analyzes a correlation between the reference stress related data and the local stress originated data and stores correlation data indicating the correlation, a measurement stress related data obtaining step that measures a Raman spectrum by irradiating energy lines on an entire area (hereinafter called as a measurement area), corresponding to the predetermined area, of a measurement specimen and obtains data (hereinafter called as measurement stress related data) regarding stress of the entire measurement area from the Raman spectrum, and a calculation step that calculates local stress originated data in the measurement area based on the correlation data and the measurement stress related data.

More concretely, it is preferable that the local stress originated data in the measurement area is mean data of the local stress. However, the local stress originated data in the measurement area is not limited to the data indicating the mean value of the local stress and may be the data indicating a minimum value or a maximum value of the local stress.

More concretely, it is preferable that the correlation data indicates a correlation between a peak shift value, a peak intensity value and a spectrum FWHM (Full Width at Half Maximum) of the Raman spectrum of the reference stress related data and those of the local stress originated data.

The peak shift value, the peak intensity value and the spectrum FWHM (Full Width at Half Maximum) may be derived as a parameter expressing the spectrum indicated by the Gauss function/Lorentz function, namely, the peak shape by approximating the Raman spectrum by the Gauss function/Lorentz function.

In addition, stress measurement apparatus in accordance with this invention is characterized by comprising a correlation data storage section that stores correlation data indicating a correlation between reference stress related data obtained from a Raman spectrum obtained by irradiating energy lines on an entire predetermined area of a reference specimen and local stress originated data as being data obtained based on local stress applying to each of multiple positions in the predetermined area, a measurement stress related data obtaining section that obtains measurement stress related data from a Raman spectrum obtained by irradiating, for example, energy lines having a spot diameter whose size is almost the same as the measurement area on an entire measurement area of a measurement specimen, and a calculation section that calculates the local stress originated data in the measurement area based on the correlation data and the measurement stress related data.

In accordance with this invention, since the correlation between the Raman spectrum obtained by irradiating the energy lines on entire predetermined area of the reference specimen and the local stress (or a value associated with the local stress such as a mean value of the local stress) applying to each portion of the predetermined area is previously obtained by the use of the reference specimen, the local stress (or a value associated with the local stress such as a mean value of the local stress) applying to the predetermined area of the measurement specimen can be obtained by making use of the correlation from the Raman spectrum obtained by conducting the Raman spectrum measurement once on the entire predetermined area of the measurement specimen.

The effects obtained by the above-mentioned method will be explained more concretely.

Since an obtained value in accordance with the stress measurement by the use of the Raman spectroscopy is an average stress value applying to an entire measurement area measured once, so called an obscure stress value, it is difficult to clearly distinguish a case wherein a big stress is applied to only a local part of the measurement area from a case wherein a certain degree of stress is applied to an entire measurement area.

On the other hand, in accordance with this invention, an accuracy of measurement can be spectacularly improved since the stress applied to the measurement area is evaluated based on the stress originated data of a local portion whose area is smaller than that of the measurement area.

In addition, in case of measuring a big area like this invention, an effect that the time required for measurement is shortened becomes especially clear. For example, in case of measuring a distribution of stress applying to a big area, conventionally each stress has to be measured for each location in the big area by conducting a mapping measurement or the like. On the other hand, in accordance with this invention, since a local stress (or a value associated with the local stress) can be obtained based on the correlation data just by measuring a Raman spectrum once from the entire big area, it becomes possible to omit a mapping measurement, thereby to substantially shorten the time required for measurement.

BRIEF DESCRIPTION OF THE DRAWINGS

FIG. 12 is a pattern laser irradiation diagram showing further different embodiment of this invention for explaining a case wherein a measurement range is changed.

DETAILED DESCRIPTION OF THE PREFERRED EMBODIMENTS

One embodiment of this invention will be explained with reference to drawings.

Figure 1:
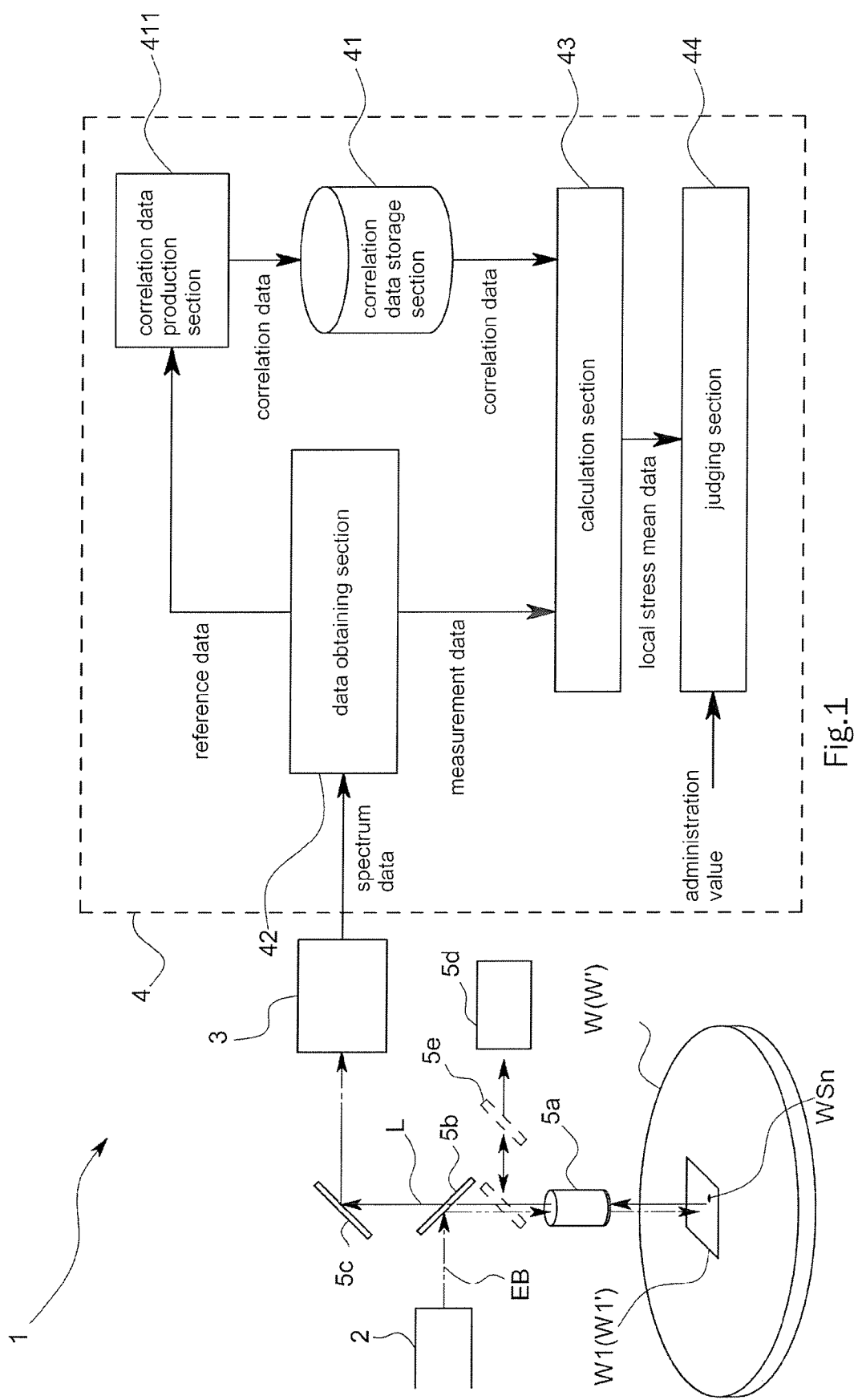
FIG. 1 is a pattern structural diagram showing an overall picture of stress measurement apparatus in accordance with one embodiment of the present claimed invention.

Stress measurement apparatus 1 in accordance with this embodiment measures stress in a measurement area of, for example, a semiconductor measurement specimen whose shape and composition are standardized in a nondestructive manner. As its pattern structural diagram is shown in FIG. 1, the stress measurement apparatus 1 comprises a laser device 2 as being an energy line irradiation device, a sensor unit 3 that receives Raman scattering light L and an information processing unit 4.

Each section will be explained in detail. The laser device 2 irradiates laser EB whose excitation wavelength is, for example, 363.8 nm as being energy lines. An irradiation object (detail will be explained later) is a predetermined area W1 of a reference specimen W, multiple (n) portions $WS_1 \sim WS_n$ in the predetermined area W1 or a measurement area W1' of a measurement specimen W'.

The sensor unit 3 receives the Raman scattering light L generated by irradiating the laser EB on the irradiation object and outputs spectrum data indicating its spectrum of the Raman scattering light L. In this embodiment, the sensor unit 3 comprises a spectroscopy section, not shown in drawings, to disperse the Raman scattering light L and multiple sensors, not shown in drawings, to detect the light intensity of each light dispersed by the spectroscopy section.

An objective lens 5*a* to focus and irradiate the laser EB on the irradiation object and to collect the Raman scattering light L from the irradiation object, a half mirror 5*b* to adjust an irradiation angle of the laser EB and a mirror 5*c* to introduce the Raman scattering light L into the sensor unit 3 are arranged between the laser device 2 and the sensor unit 3. A referential code 5*d* is a camera for optical observation used for verifying a position where the laser EB is irradiated, and a referential code 5*e* is a second half mirror to introduce the light into the camera 5*d*, and each of which is arranged detachably on an optical path.

The information processing unit 4 to process data output from the sensor unit 3 is a so-called computer comprising, for example, a CPU, a memory or other peripheral devices and produces functions of the following each section by operating the CPU in accordance with a program stored in the memory.

More specifically, the information processing unit 4 comprises a correlation data storage section 41 that stores correlation data indicating a correlation between the reference stress related data obtained from the spectrum data of the predetermined area W1 and local stress originated data obtained from the spectrum data of the multiple portions $WS_1 \sim WS_n$, a data obtaining section 42 that obtains data regarding the stress from the spectrum data of the reference specimen W and the measurement specimen W', a calculation section 43 that calculates local stress originated data in the measurement area W1' based on measurement stress related data obtained from the spectrum data of the measurement specimen W' and the correlation data, and a judging section 44 that compares a value of the local stress originated data calculated by the calculation section 43 with a previously set administration value and judges whether or not the value of the local stress originated data falls within a range of the administration value.

The correlation data corresponds to a so-called analytical curve, and in order to produce the correlation data, the information processing unit 4 further comprises a correlation data production section 411 that produces the correlation data and writes the correlation data into the correlation data storage section 41.

Figure 4:
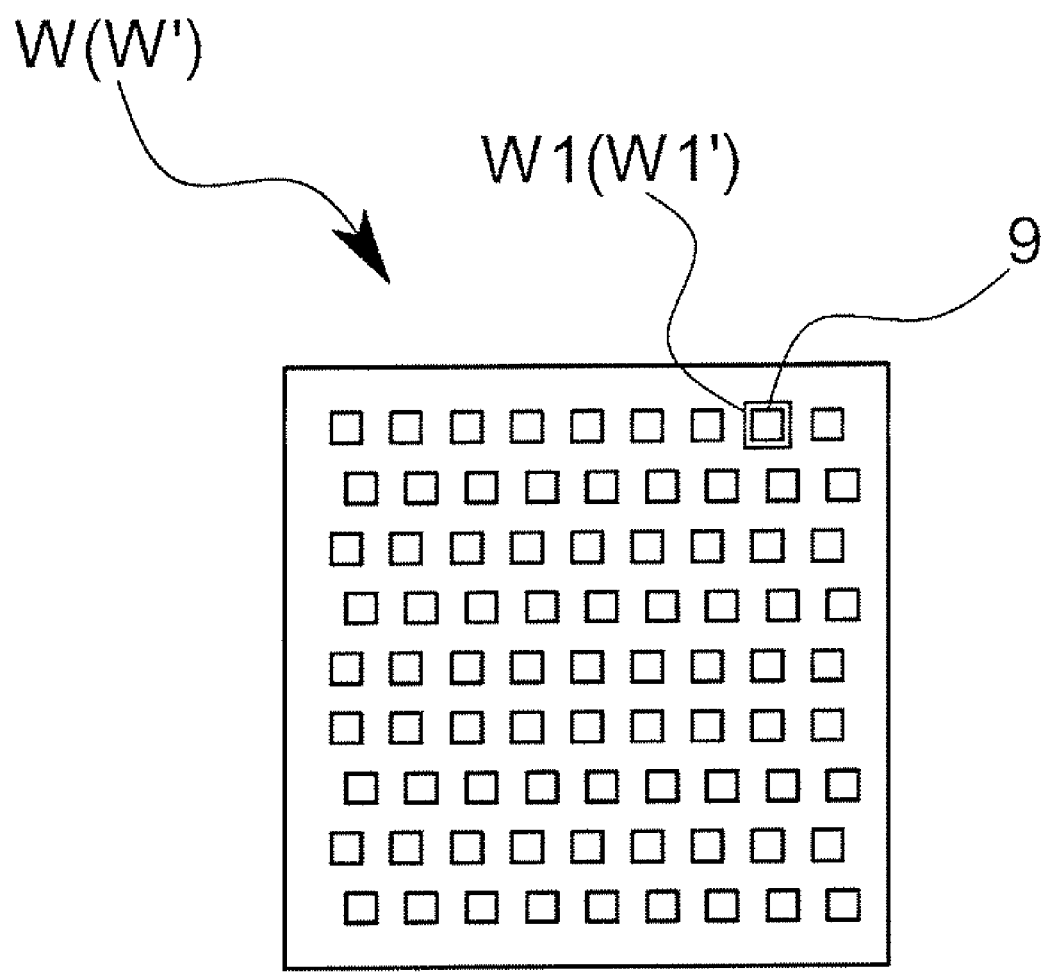
FIG. 4 is a pattern plane view showing a reference specimen in this embodiment.

The reference specimen W and the measurement specimen W' as being the above-mentioned irradiation object will be explained. A composition and a structure of the reference specimen W are the same as those of the measurement specimen W', and multiple rectangle convex micro-structures 9 are formed in parallel with forming grooves on a surface of a flat plate made of Si by means of etching, as shown in FIG. 4. In this embodiment the micro-structure is, for example, a shallow trench isolation structure (STI).

Next, an operation of the stress measurement apparatus 1 of the above-mentioned arrangement will be explained with reference to flow chars in FIG. 2 and FIG. 3.

Figure 5:
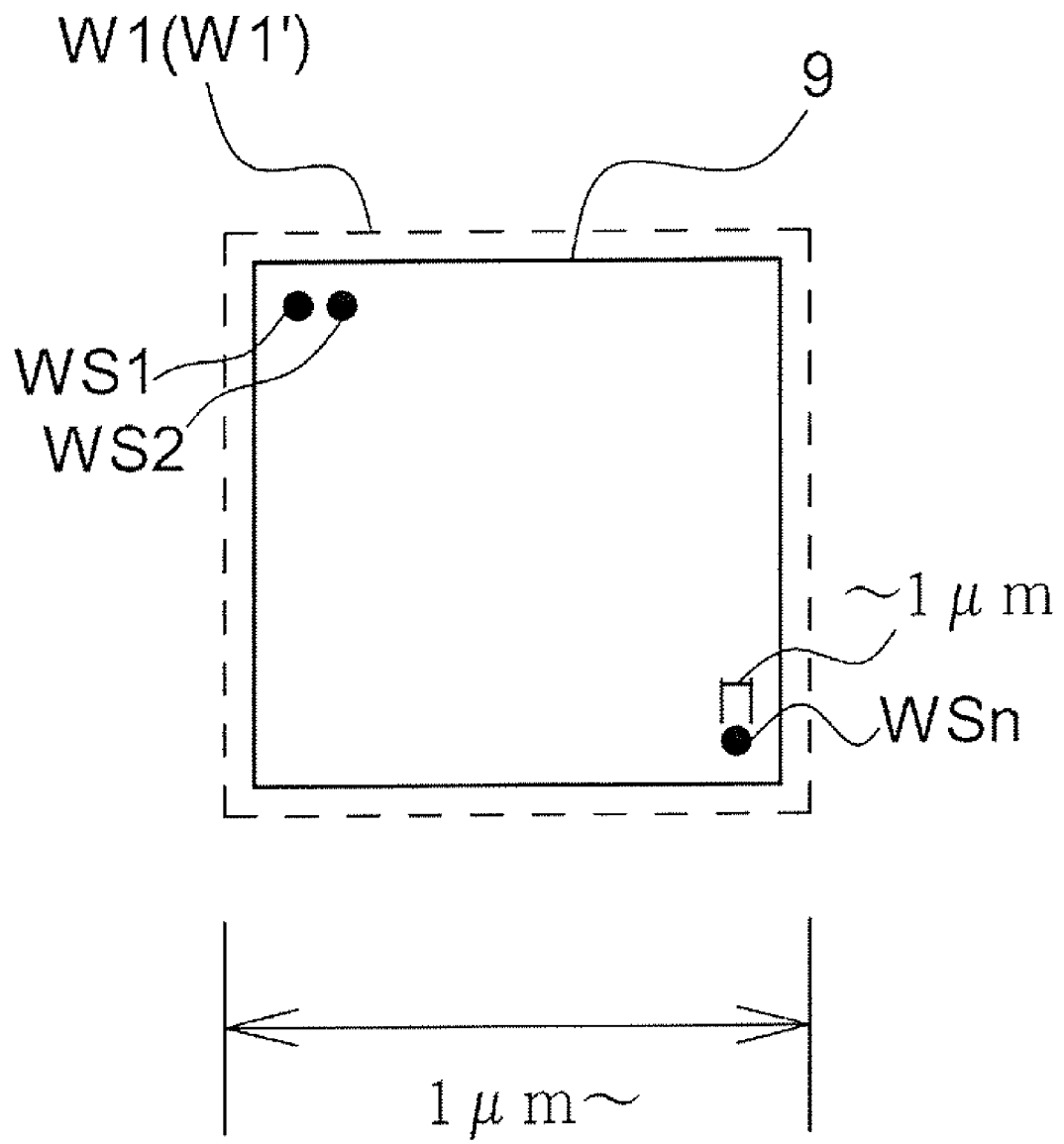
FIG. 5 is a partially magnified view showing a predetermined area of the reference specimen and multiple local portions of the predetermined area in this embodiment.

First, the laser EB is irradiated on the entire (its magnified view is shown in FIG. 5) predetermined area W1, containing about one piece of the micro-structure 9, of the reference specimen W by the laser device 2. The sensor unit 3 receives the Raman scattering light L from the predetermined area W1, the data obtaining section 42 receives Raman spectrum data as being its output signal and the reference stress related data as being data regarding the stress of the entire predetermined area W1 is calculated (FIG. 2, step S11).

The reference stress related data in this embodiment indicates a shape of the Raman spectrum and is expressed as, for example, $[v_{large}, A_{large}, \omega_{large}]$.

In this embodiment, $v_{large}$ is a peak shift value, $A_{large}$ is a peak intensity value, and $\omega_{large}$ is a spectrum FWHM (Full Width at Half Maximum) of the Raman spectrum. The reference stress related data may be either one or two of the above, and it may be other value or data indicating the shape itself of the Raman spectrum.

As a method for calculating $v_{large}, A_{large}, \omega_{large}$, the data obtaining section 42 approximates the Raman spectrum by multiple (two) spectrum elements expressed by, for example, the Gauss function/the Lorentz function or the asymmetric Gauss function and calculates $v_{large}, A_{large}, \omega_{large}$ based on its result.

Next, stress distribution of the predetermined area W1 is mapping-measured. More specifically, for example, the laser spot diameter is reduced (smaller than about 1 μm) and the laser EB is irradiated on each of n pieces of the portions (hereinafter called also as local areas) $WS_1 \sim WS_n$ of the predetermined area W1 (refer to FIG. 5).

Figure 2:
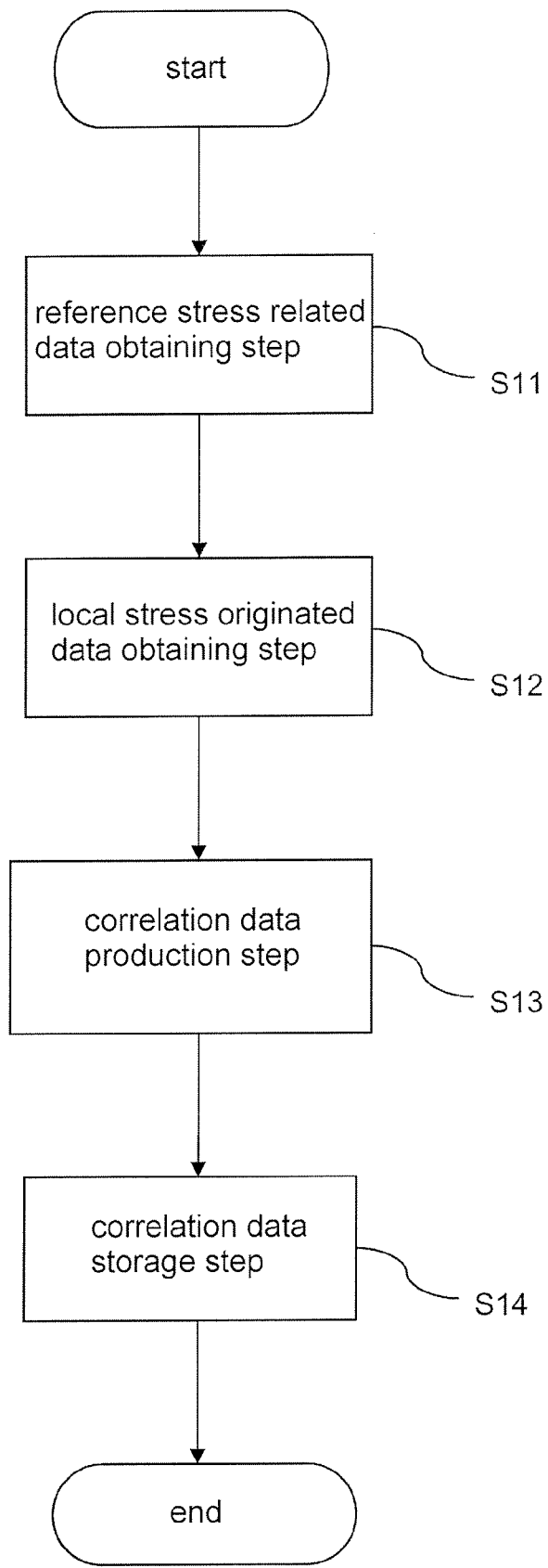
FIG. 2 is a flow chart showing a flow until correlation data is stored in this embodiment.

Then, similar to the above-mentioned, the data obtaining section 42 calculates the local stress originated data as being data regarding stress applied to each local areas $WS_1 \sim WS_n$ based on the Raman spectrum data obtained from each local areas $WS_1 \sim WS_n$ (FIG. 2, step S12).

The local stress originated data in this embodiment indicates a shape of the Raman spectrum obtained from each local areas $WS_1 \sim WS_n$ and is expressed as, for example, $[v_{average}, A_{average}, \omega_{average}]$. The local stress originated data may be either one or two of the above, and it may be other value or data indicating the shape itself of the Raman spectrum.

Figure 6:
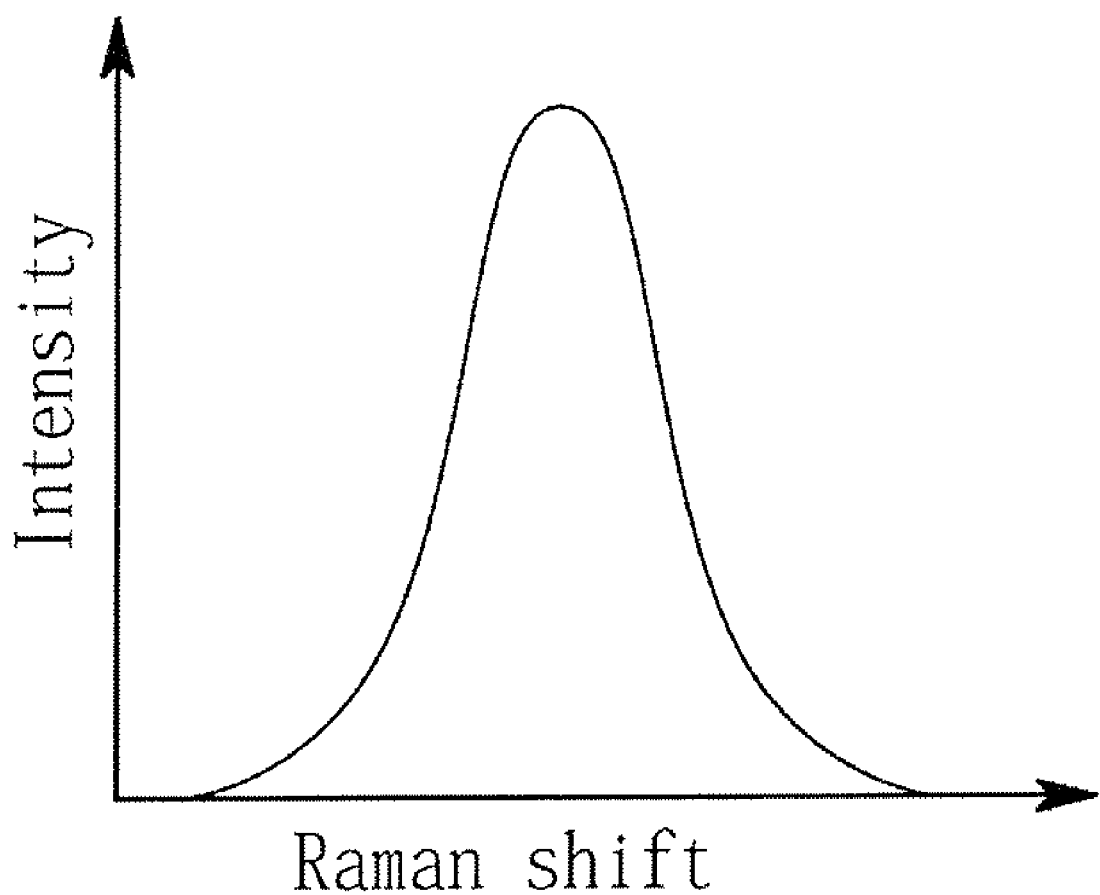
FIG. 6 is an example view showing a spectrum obtained at a certain portion in this embodiment.

In this embodiment, $v_{average}$ is a mean value of the peak shift values, $A_{average}$ is a mean value of the peak intensity values, and $\omega_{average}$ is a mean value of the spectrum FWHM (Full Width at Half Maximum) of each local area $WS_1 \sim WS_n$. Similar to a case of the above-mentioned reference stress related data, the peak shift values, the peak intensity values and the spectrum FWHM (Full Width at Half Maximum) are calculated based on a result: the Raman spectrum is approximated by multiple (two) spectrum elements expressed by, for example, the Gauss function/the Lorentz function or the asymmetric Gauss function. An example of the spectrum obtained at a certain local area $WS_i$ is shown in FIG. 6.

In this embodiment, for mapping, the laser EB is irradiated on each of the multiple local areas $WS_1 \sim WS_n$ with changing the angle of the laser EB by the use of the half mirror 5b. In addition, a stage that supports the reference specimen W may be moved for mapping. Furthermore, in order to measure the stress of each local area $WS_1 \sim WS_n$, other stress measurement apparatus such as the CBED may be used in addition to the Raman spectroscopy.

Then the stress measurement for the entire predetermined area W1 and a more accurate local stress measurement for the predetermined area W1 by mapping are conducted on each of the multiple (m pieces of) reference specimens $W_k$ (k is an integer from 1 to m) to which different stress is applied.

Next, the correlation data production section 411 produces correlation data indicating a correlation between the reference stress related data $[v_{large}, A_{large}, \omega_{large}]_k$ and the local stress originated data $[v_{average}, A_{average}, \omega_{average}]_k$ based on the reference stress related data $[v_{large}, A_{large}, \omega_{large}]_k$ and the local stress originated data $[v_{average}, A_{average}, \omega_{average}]_k$ each of which is obtained from m pieces of the reference specimen $W_k$ (FIG. 2, step S13). This is based on that the inventor of this invention found there was a certain correlation between the Raman spectrum obtained from the predetermined area W1 and the Raman spectrum obtained from the local areas $WS_1 \sim WS_n$.

The step S11~the step S13 will be explained more concretely with reference to the following example.

Figure 7:
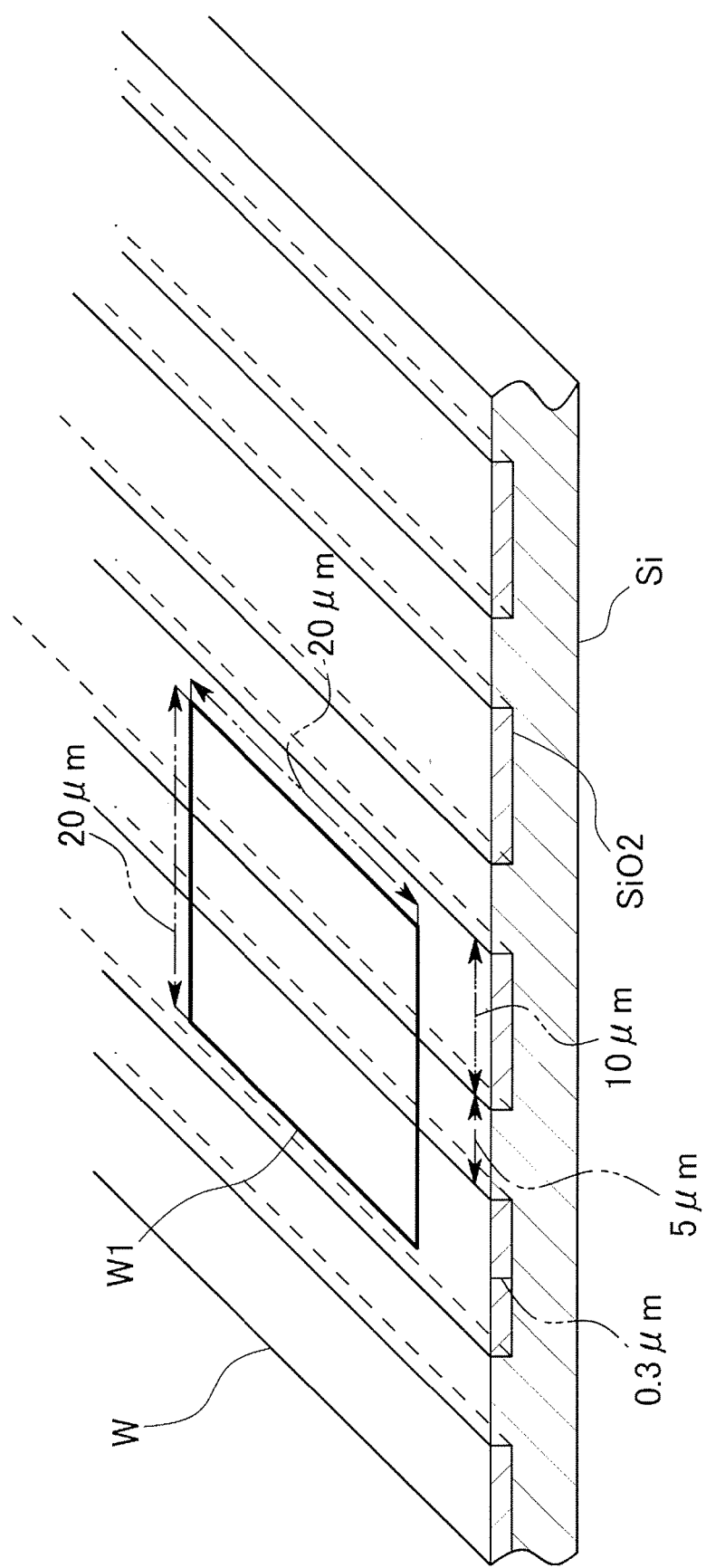
FIG. 7 is a pattern perspective view showing a specimen used in this embodiment.

The reference stress related data was calculated by irradiating the laser EB whose wavelength is 488.0 nm on the entire predetermined area W1 of 20×20 μm of the reference specimen W shown in FIG. 7. A macro spot is generated with the scanning of the laser light by galvanometer mirror (refer to FIG. 11) and obtaining the Raman spectrum data with a scanning speed of 200 μm/sec and a measurement time of 4 sec (step S11).

Next, the local stress originated data was calculated by irradiating the laser EB whose wavelength is 488.0 nm on the same predetermined area W1 of the same reference specimen W by a micro spot with a reduced laser spot diameter under the following condition and obtaining the Raman spectrum data from each measurement point (step S12).

Data obtaining time for one point: 10 sec (5 sec×2)

Measurement area: 20×20 μm

Measurement step: 2 μm

Total number of measurement point: 121

Measurement time: 1210 sec

The measurement position is fed by a stage.

Figure 8:
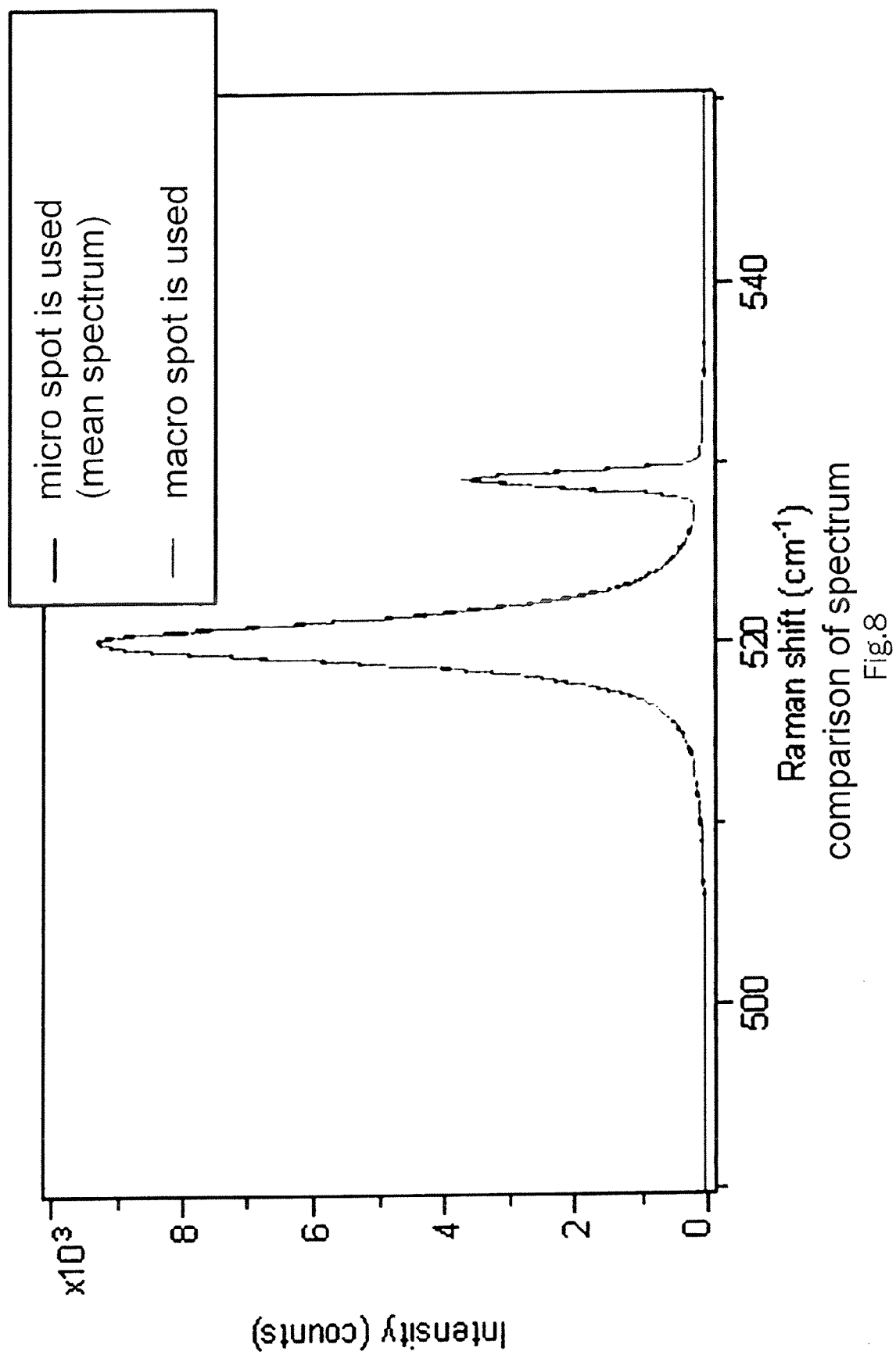
FIG. 8 is a graph showing a correlation between reference stress related data and local stress originated data obtained by irradiating lasers whose wavelength is 488.0 nm.

The reference stress related data and the local stress originated data obtained by irradiating the laser EB whose wavelength is 488.0 nm were compared in the following table 1. In addition, correlation data indicating a correlation between the reference stress related data and the local stress originated data was produced based on the reference stress related data and the local stress originated data (step S13). A graph indicating the correlation is shown in FIG. 8.

TABLE 1

|  | Peak shift (cm$^{-1}$) | Peak intensity (counts) | FWHM (Full Width at Half Maximum) (cm$^{-1}$) |
| --- | --- | --- | --- |
| Reference stress related data | $v_{large}$ 520.746 | $A_{large}$ 9264.0 | $\omega_{large}$ 2.768 |
| Local stress originated data | $v_{average}$ 520.757 | $A_{average}$ 9432.2 | $\omega_{average}$ 2.774 |

In addition, the reference stress related data was calculated by irradiating the laser EB whose wavelength is 363.8 nm on the entire predetermined area W1 of 20×20 μm of the reference specimen W shown in FIG. 7 by a macro spot and obtaining the Raman spectrum data with a scanning speed of 200 μm/sec and a measurement time of 4 sec (step S11).

Next, the local stress originated data was calculated by irradiating the laser EB whose wavelength is 363.8 nm on the same predetermined area W1 of the same reference specimen W by a micro spot under the following condition and obtaining the Raman spectrum data from each measurement point (step S12).

Data obtaining time for one point: 4 sec (2 sec×2)

Measurement area: 20×20 μm

Measurement step: 2 μm

Total number of measurement point: 121

Measurement time: 484 sec

The measurement position is fed by a stage.

Figure 9:
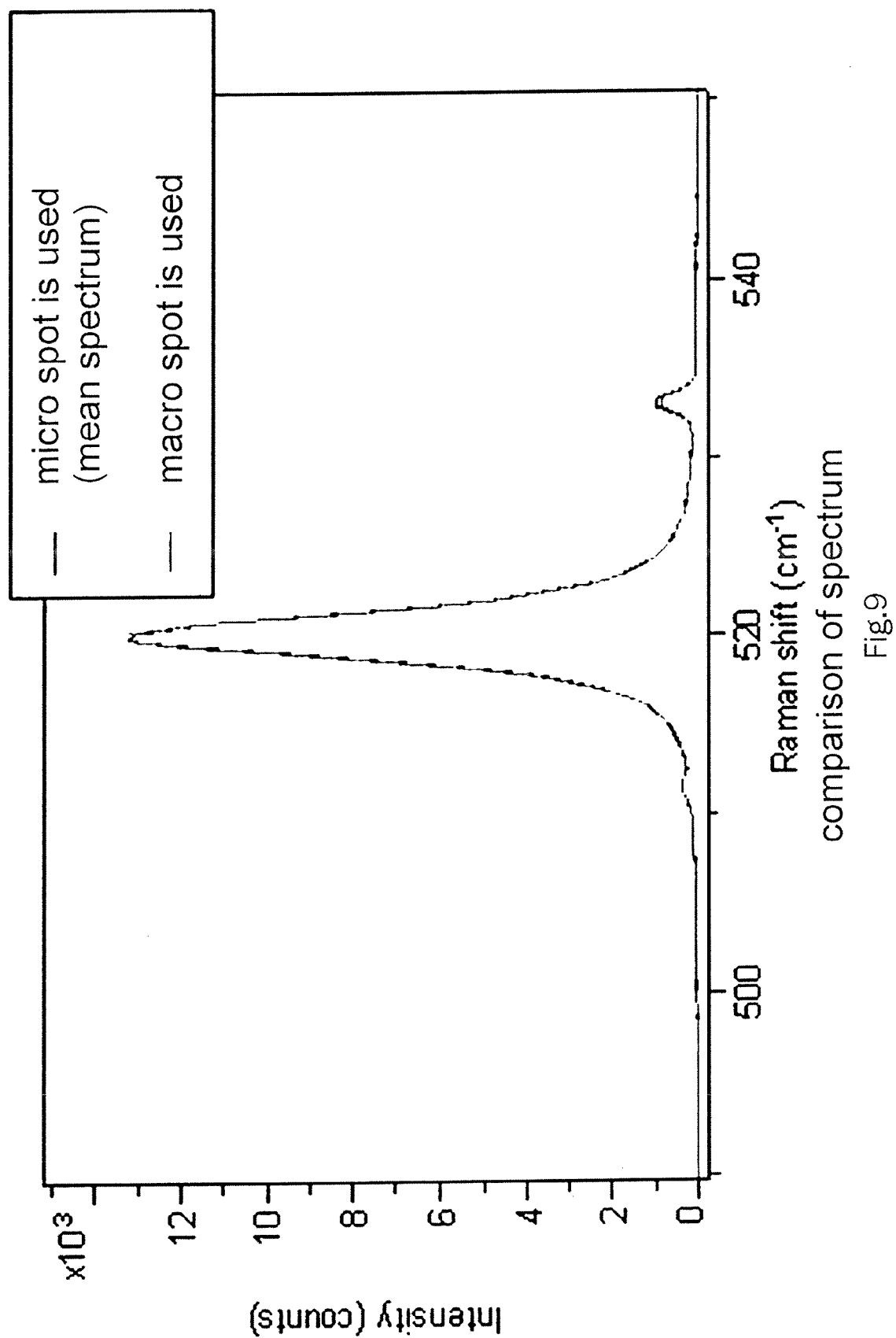
FIG. 9 is a graph showing a correlation between reference stress related data and local stress originated data obtained by irradiating lasers whose wavelength is 363.8 nm.

The reference stress related data and the local stress originated data obtained by irradiating the laser EB whose wavelength is 363.8 nm were compared in the following table 2. In addition, correlation data indicating a correlation between the reference stress related data and the local stress originated data was produced based on the reference stress related data and the local stress originated data (step S13). A graph indicating the correlation is shown in FIG. 9.

TABLE 2

|  | Peak shift (cm$^{-1}$) | Peak intensity (counts) | FWHM (Full Width at Half Maximum) (cm$^{-1}$) |
| --- | --- | --- | --- |
| Reference stress related data | $v_{large}$ 520.040 | $A_{large}$ 13461.1 | $\omega_{large}$ 3.135 |
| Local stress originated data | $v_{average}$ 520.068 | $A_{average}$ 13341.0 | $\omega_{average}$ 3.116 |

Figure 10:
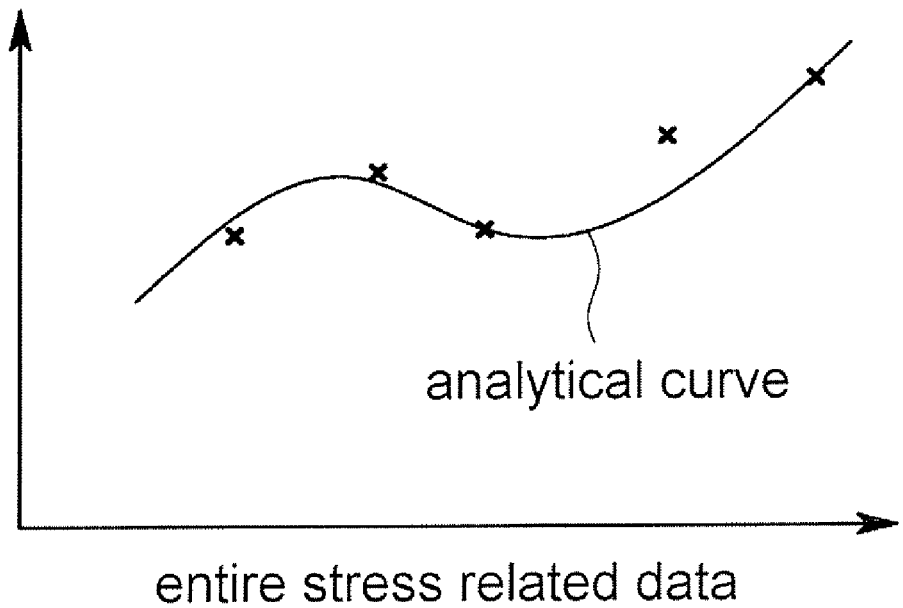
FIG. 10 is a conceptual diagram showing correlation data (analytical curve) in this embodiment.

The obtained correlation data is stored in the correlation data storage section 41 (FIG. 2, step S14). An image of the correlation data (the analytical curve) is shown in FIG. 10. In FIG. 10, the reference stress related data and the local stress originated data having three variables are depicted on a horizontal axis and a vertical axis as if it were one-dimension, however, it is just for helping understanding.

Figure 3:
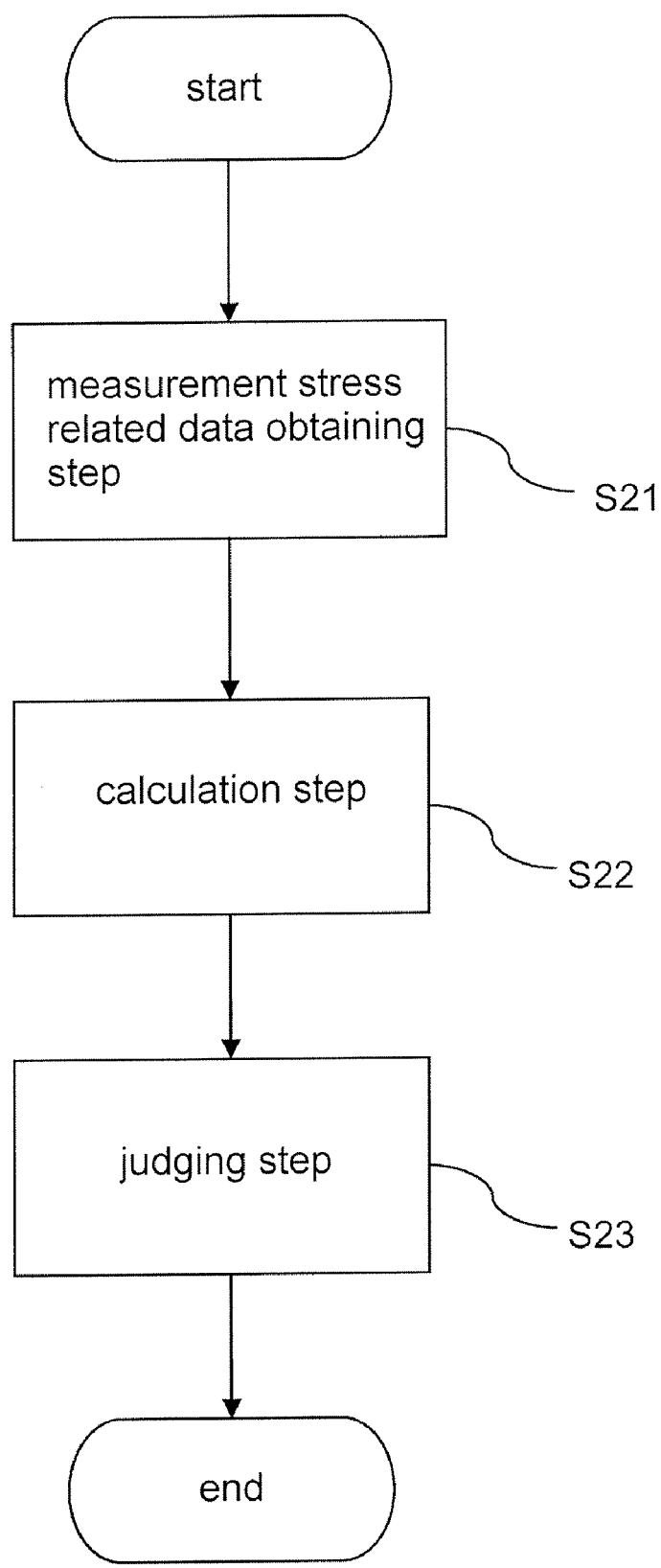
FIG. 3 is a flow chart showing a flow until local stress originated data of a measurement area is calculated in this embodiment.

After obtaining the correlation data with the above-mentioned procedure, the spectrum data of the measurement specimen W' is obtained and its local stress originated data is calculated in accordance with the procedures in FIG. 3. In this embodiment, the measurement specimen W' is a specimen whose shape and composition are the same as those of the reference specimen W and whose stress is unknown.

First, similar to the step S11, the laser EB having a laser spot diameter generally the same as that of the predetermined area W1' is irradiated on the predetermined area W1' of the measurement specimen W'. Then the sensor unit 3 receives the Raman scattering light L generated at this time and the data obtaining section 42 receives the Raman spectrum data as being its output signal and calculates the measurement stress related data as being data regarding the stress of the entire predetermined area W1' (step S21).

The measurement stress related data formally corresponds to the reference stress related data formally, and in this embodiment, it indicates a shape of the Raman spectrum. More specifically, it comprises a combination of three values; a peak shift value, a peak intensity value and a spectrum FWHM (Full Width at Half Maximum) of the Raman spectrum.

Then the calculation section 43 calculates the local stress originated data, more specifically, the mean data of the local stress in the reference specimen, of the measurement specimen W' by checking the measurement stress related data obtained in the above-mentioned step S21 against the correlation data (the analytical curve, refer to FIG. 10) stored in the correlation data storage section 41 in the above-mentioned step S14 (step S22).

In this embodiment, the judging section 44 compares the mean data value of the calculated local stress with the stress administration value that has been previously set, and if the mean data value falls within a certain range of the stress administration value, it is judged as the mean data value satisfies the stress administration value, and otherwise judged as the mean data does not satisfy the stress administration value and then displays its result (step S23).

In accordance with the stress measurement apparatus 1 of this arrangement, since it is possible to calculate each local stress (or a value associated with the local stress like the above-mentioned mean value) that applies to the measurement area W1' only by comparing the data regarding the stress obtained by the Raman measurement conducted once by the use of the laser EB having a spot diameter that is generally the same as that of the measurement area W1' with the analytical curve (the correlation data) that has been previously made, the stress measurement apparatus 1 can measure stress more accurately than a conventional apparatus can. In addition, all the time required for measurement in accordance with the stress measurement apparatus 1 is the time while it takes to conduct the Raman measurement once and to calculate the stress, and it is almost the same as the time required for a conventional Raman measurement. As a result, since nondestructive measurement on the measurement specimen can be conducted in a short period of time, it is possible to utilize this measurement for a process line. In addition, since the spot diameter can be easily adjusted in accordance with a size of the measurement area W1', it becomes possible to apply the stress measurement apparatus 1 to the measurement area W1' of various sizes.

Furthermore, since the judging section 44 can administrate the stress during a process, it is possible to eliminate, for example, the measurement specimen W' to which an excessive stress is applied during an inline process.

The present claimed invention is not limited to the above-mentioned embodiment.

For example, the energy line irradiating on the measuring object is not limited to the ultraviolet laser, and may be visible lasers.

The irradiation angle of the laser EB may be any as far as the Raman scattering light L can be obtained from the reference specimen W and the measurement specimen W', and an optical system may be adjusted to conduct Raman measurement such that the angle of the half mirror is changed so as to make the irradiation angle at a desired angle.

The micro-structure contained in a specimen to be the measuring object is not limited to the micro-structure made of Si, and may be represented by various micro-structures such as NiSi, a SiN chemical compound formed to cover a transistor, SiGe, strained Si, SOI, SGOI, TiN, $HfO_2$, HfSiON, SiC, LOCOS, GaN, GaAs and InSb.

In addition, the specimen as being the measuring object is not necessarily contain micro-structures, and may be, for example, a tabular specimen without any micro-structures.

The parameter expressing the peak shape is not limited to the peak shift and the peak intensity and the spectrum FWHM (Full Width at Half Maximum) of the spectrum element, and may be any as far as it expresses the shape of the Raman spectrum.

In order to calculate the correlation data, it is not necessary to obtain the spectrum data from multiple reference specimens each of which different stress is applied to, and the Raman spectrum data may be obtained from different areas of a single reference specimen.

As a device to obtain the data of the entire predetermined area of the reference specimen, for example, the XRD device may be used. As a device to obtain the data of the local portion among the predetermined area of the reference specimen, it is possible to use a measurement method such as the CBED, the EBSD (Electron Backscatter Diffraction), the near-field Raman, the NBD (nano Beam Diffraction) and the CL (Cathode Luminescence) that can obtain the data with higher resolution than the Raman measurement does. This is because it does not matter that a destructive inspection is conducted and it takes time.

Figure 11:
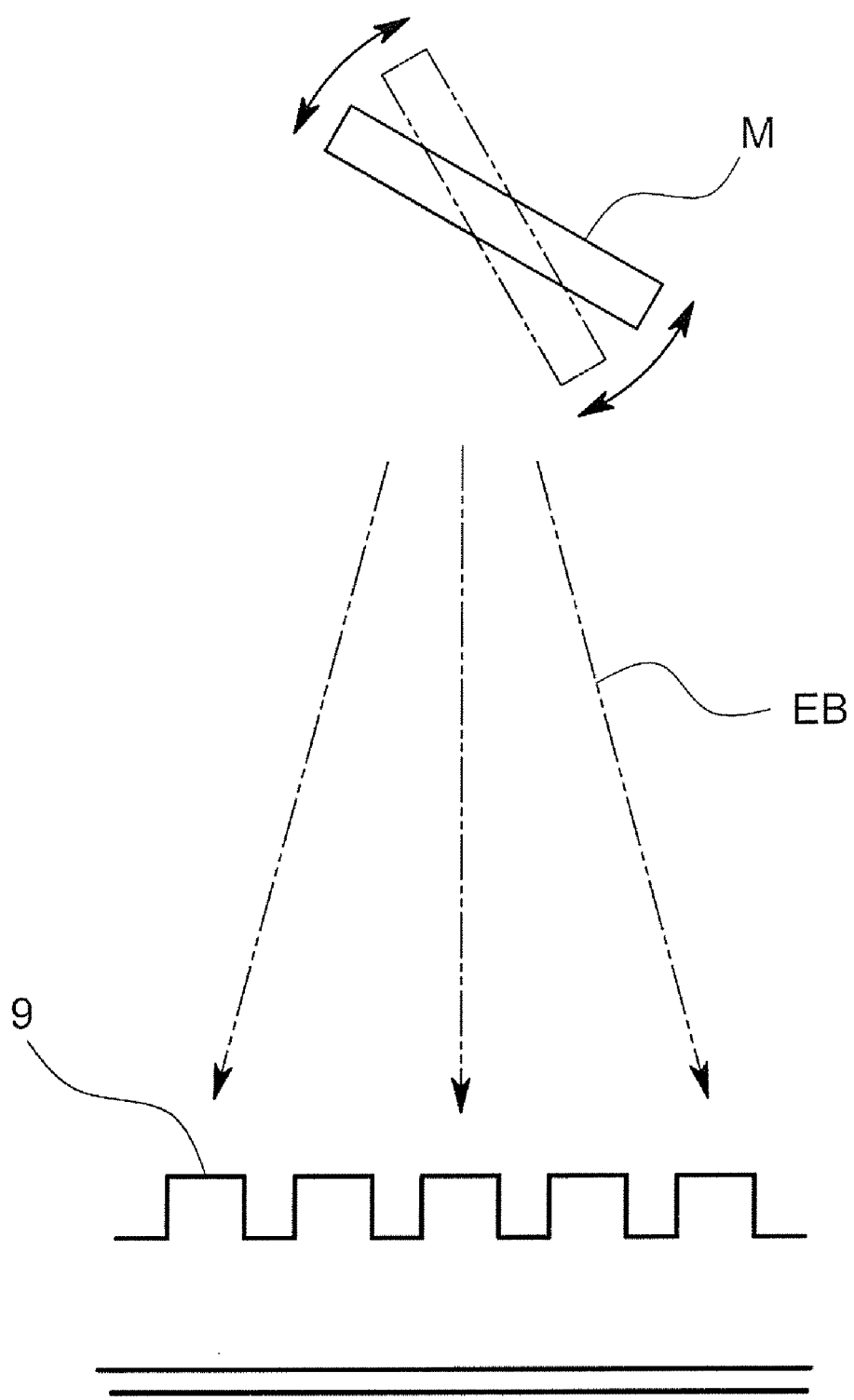
FIG. 11 is a pattern diagram showing other embodiment of this invention for explaining measurement by the use of a galvanometer mirror.

A range of the specimen to be measured once may be adjusted by expanding or shrinking the laser irradiation area and it may be adjusted by expanding or shrinking the light receiving range of the Raman light by the use of an optical system in a light receiving side. For example, as an example of adjusting the measurement range by the laser irradiation diameter (a spot diameter), in case of using the objective lens like the above-mentioned embodiment, an arrangement wherein multiple objective lenses each of whose focal length differs are prepared and switched or an arrangement wherein a distance between the objective lens and the specimen is set to be variable may be conceived. In addition to this, the laser irradiation area may be expanded or shrunk by changing a scan range by utilizing a galvanometer mirror M as shown in FIG. 11. In case of using, for example, a confocal optical system as an example of adjusting the measurement range by means of the optical system in the light receiving side, it is possible to adjust the measurement range by expanding or shrinking the aperture of the confocal hole. The confocal hole is arranged in front of the sensor unit 3, for example, shown in FIG. 1. Especially small measurement area can be realized by a near-field optical system or the like.

In case that the Raman measurement is conducted once on multiple micro-structures 9 contained in the measurement area by making use of switching the objective lens or adjusting the aperture of the confocal hole so as to enlarge the measurement area without moving an optical axis of the laser EB, it becomes possible to evaluate the measurement area more accurately by considering an effect caused by a difference of distance between each focal distance of multiple micro-structures 9 and the optical axis 6 as shown in FIG. 12(a). Then the calculation section 43 obtains the measurement stress related data per one micro-structure 9 by conducting a formula manipulation by the use of a fact that a number, a configuration interval and the Raman spectrum intensity of the micro-structures 9 in the measurement area show the Gaussian distribution, and calculates the stress of the measurement area by comparing the obtained measurement stress related data with the correlation data.

Furthermore, it is more preferable if a number of the micro-structures 9 contained in the measurement area and a ratio of the area of the micro-structures 9 to an area of the measurement area are considered. More concretely, it becomes possible to calculate the stress applying to the measurement area more accurately if the calculation section 43 obtains measurement stress related data per one micro-structure 9 from the Raman spectrum obtained from one of the micro-structures 9 estimated with including the number of the micro-structures 9, the ratio of the area of the micro-structures 9 to the area of the measurement area, the peak intensity and the spectrum FWHM (Full Width at Half Maximum) of the parameter and compares the obtained measurement stress related data with the correlation data.

In addition, in case that Raman measurement is conducted on the predetermined area of the reference specimen containing one micro-structure 9 by making use of switching the objective lens or adjusting the aperture of the confocal hole in order to produce the correlation data (refer to FIG. 12 (b)), it becomes possible to obtain more accurate data if a difference of the focal depth of the laser light is taken into consideration. At this time, it is better to estimate a change of the spectrum due to the difference of the focal depth and its estimated change is reflected on the result of the Raman measurement. For example, if the change of the spectrum due to the difference of the focal depth is subtracted from the result of the Raman measurement obtained by the use of the laser lights having the spot diameter almost the same as that of the predetermined area of the reference specimen, it becomes possible to obtain more accurate evaluation (an accurate correlation data) than a case wherein no effect is considered.

In addition, a part or all of the above-mentioned embodiment or the modified embodiment may be appropriately combined. This invention is not limited to the above-mentioned embodiment and it is a matter of course that this invention may be variously modified without departing from the concept of the invention.

The invention claimed is:

1. Stress measurement method comprising
a reference stress related data obtaining step that measures a Raman spectrum by irradiating energy lines on an entire predetermined area of a reference specimen, and obtains data (hereinafter called as reference stress related data) regarding stress of the entire predetermined area from the Raman spectrum,
a local stress originated data obtaining step that measures local stress applying to each of multiple positions in the predetermined area, and obtains local stress originated data as being data that can be obtained based on the local stress,
a correlation data storage step that analyzes a correlation between the reference stress related data and the local stress originated data, and stores correlation data indicating the correlation,
a measurement stress related data obtaining step that measures a Raman spectrum by irradiating energy lines on an entire area (hereinafter called as a measurement area), corresponding to the predetermined area, of a measurement specimen, and obtains data (hereinafter called as measurement stress related data) regarding stress of the entire measurement area from the Raman spectrum, and a calculation step that calculates local stress originated data in the measurement area based on the correlation data and the measurement stress related data.

2. The stress measurement method described in claim 1, wherein the local stress originated data in the measurement area is mean data of the local stress.

3. The stress measurement method described in claim 1, wherein the correlation data indicates a correlation between a peak shift value, a peak intensity value and a spectrum FWHM (Full Width at Half Maximum) of the Raman spectrum of the reference stress related data and those of the local stress originated data.

4. Stress measurement apparatus comprising a correlation data storage section that stores correlation data indicating a correlation between reference stress related data obtained from a Raman spectrum obtained by irradiating energy lines on an entire predetermined area of a reference specimen and local stress originated data as being data obtained based on local stress applying to each of multiple positions in the predetermined area, a measurement stress related data obtaining section that obtains measurement stress related data from a Raman spectrum obtained by irradiating energy lines on an entire measurement area of a measurement specimen, and a calculation section that calculates the local stress originated data in the measurement area based on the correlation data and the measurement stress related data.

5. The stress measurement apparatus described in claim 4, and further comprising a judging section that compares a value of the local stress originated data calculated by the calculation section with a previously set administration value and judges whether the value of the local stress originated data falls within a range of the administration value.

6. The stress measurement method described in claim 2, wherein the correlation data indicates a correlation between a peak shift value, a peak intensity value and a spectrum FWHM (Full Width at Half Maximum) of the Raman spectrum of the reference stress related data and those of the local stress originated data.

* * * * *